US008637266B2

(12) United States Patent
Barnes et al.

(10) Patent No.: US 8,637,266 B2
(45) Date of Patent: Jan. 28, 2014

(54) ANTI BONE-LOSS AND ANTI ATTACHMENT-LOSS EFFECTS OF AN ORAL COMPOSITION

(75) Inventors: Virginia Barnes, Ringoes, NJ (US); Harsh M. Trivedi, Hillsborough, NJ (US); Wei Wang, East Brunswick, NJ (US); Tao Xu, Newton, MA (US); Emi Shimizu, North Brunswick, NJ (US); Nicola C. Partridge, New York, NY (US)

(73) Assignee: Colgate-Palmolive Company, New York, NY (US)

( * ) Notice: Subject to any disclaimer, the term of this patent is extended or adjusted under 35 U.S.C. 154(b) by 117 days.

(21) Appl. No.: 13/262,027

(22) PCT Filed: Apr. 1, 2010

(86) PCT No.: PCT/US2010/029670
§ 371 (c)(1),
(2), (4) Date: Sep. 29, 2011

(87) PCT Pub. No.: WO2010/115031
PCT Pub. Date: Oct. 7, 2010

(65) Prior Publication Data
US 2012/0107843 A1 May 3, 2012

Related U.S. Application Data

(60) Provisional application No. 61/165,685, filed on Apr. 1, 2009.

(51) Int. Cl.
*G01N 33/53* (2006.01)
(52) U.S. Cl.
USPC .................................. 435/7.4; 424/94.1
(58) Field of Classification Search
None
See application file for complete search history.

(56) References Cited

U.S. PATENT DOCUMENTS

| | | | |
|---|---|---|---|
| 3,538,230 | A | 11/1970 | Pader et al. |
| 4,358,437 | A | 11/1982 | Duke |
| 5,288,480 | A | 2/1994 | Gaffar et al. |
| 5,578,295 | A | 11/1996 | Francis et al. |
| 5,703,123 | A | 12/1997 | Pelzer et al. |
| 7,005,225 | B2 | 2/2006 | Qian et al. |
| 7,005,255 | B2 | 2/2006 | Kaddurah-Daouk et al. |
| 7,329,489 | B2 | 2/2008 | Kaddurah-Daouk et al. |
| 7,550,258 | B2 | 6/2009 | Kaddurah-Daouk et al. |
| 7,635,556 | B2 | 12/2009 | Kaddurah-Daouk et al. |
| 2004/0224876 | A1 | 11/2004 | Jost-Price et al. |
| 2005/0014132 | A1 | 1/2005 | Kaddurah-Daouk et al. |
| 2005/0113345 | A1 | 5/2005 | Chow et al. |
| 2006/0134676 | A1 | 6/2006 | Kaddurah-Daouk et al. |
| 2006/0134677 | A1 | 6/2006 | Kaddurah-Daouk et al. |
| 2006/0134678 | A1 | 6/2006 | Kaddurah-Daouk et al. |
| 2006/0141421 | A1 | 6/2006 | Braunecker et al. |
| 2007/0072203 | A1 | 3/2007 | Kaddurah-Daouk et al. |
| 2007/0160544 | A1 | 7/2007 | Sreenivasan |
| 2008/0027146 | A1 | 1/2008 | Fiorellini et al. |

FOREIGN PATENT DOCUMENTS

| | | |
|---|---|---|
| EP | 0528468 | 2/1993 |
| EP | 10578809 | 12/2000 |
| EP | 1210928 | 6/2002 |
| EP | 1925292 | 5/2008 |
| GB | 2401865 | 11/2004 |
| WO | WO 95/13094 | 5/1995 |
| WO | WO 97/47282 | 12/1997 |
| WO | WO 01/48481 | 7/2001 |
| WO | WO 01/55386 | 8/2001 |
| WO | WO 01/85116 | 11/2001 |
| WO | WO 2005/039504 | 5/2005 |
| WO | WO 2005/057222 | 6/2005 |
| WO | WO 2005/103071 | 11/2005 |
| WO | WO 2008/093072 | 7/2008 |
| WO | WO 2009/048841 | 4/2009 |

OTHER PUBLICATIONS

Afflitto et al., 1989, "Salivary and plaque triclosan levels after brushing with a 0.3% triclosan/copolymer/NaF dentifrice," Amer. J. Dent. 2:207-210.
Akalin et al., 2007, "Lipid Peroxidation Levels and Total Oxidant Status in Serum, Saliva and Gingival Crevicular Fluid in Patients with Chronic Periodontitis," J. Clin. Periodontol. 34(7):558-265.
Armitage, 2004, "Analysis of Gingival Crevice Fluid and Risk of Progression of Periodontitis," Periodontal. 34:109-119.
Back et al., 2007, "Increased Leukotrienc Concentrations in Gingival Crevicular Fluid from Subjects with Periodontal Disease and Atherosclerosis," Atherosclerosis 193(2):389-394.
Bergamini et al., 2004, "Oxygen, Reactive Oxygen Species and Tissue Damage" Curr. Pharm. Des. 10(14):1611-1626.
Berry et al., 2004, "Xanthine Oxidoreductase and Cardiovascular Disease: Molecular Mechanisms and Pathophysiological Implications," J. Physiol. 555(Pt. 3):589-606.
Bodet et al., 2005, "Modulation of cytokine production by Porphyromonas gingivalis in a macrophage and epithelial cell co-culture model," Microbes & Infect. 7(3):448-456.
Brantzaeg et al., 1992. "Compartmentalization of lipopolysaccharide production correlates with clinical presentation in meningococcal disease," J. Infect. Dis. 166(3):650-652.
Bunnell et al., 2000, "A lipid A analog, E5531, blocks the endotoxin response in human volunteers with experimental endotoxemia," Crit. Care Med. 28(8):2713-2720.
Cannon et al., 2008, "Salivary Metabonomics: A New Objective Measure in Oral Care," Poster 14, 8th European Symposium on Saliva, May 14-17, 2008, The Netherlands.
Chapple et al., 2002, "Glutathione in Gingival Crevicular Fluid and Its Relation to Local Antioxidant Capacity in Periodontal Health and Disease," Mol. Pathol. 55(6):367-373.

(Continued)

*Primary Examiner* — Michael Pak
(74) *Attorney, Agent, or Firm* — Nikhil A. Heble (57) ABSTRACT

Methods for identifying compounds useful for treating diseases and conditions of the oral cavity are described herein.

11 Claims, 3 Drawing Sheets

(56) References Cited

OTHER PUBLICATIONS

Ciantar et al., 2002, "Development of an in vitro Microassay for Glucose Quantification in Submicrolitre Volumes of Biological Fluid," J. Periodontal Res. 37(2):79-85.

El Moudni et al., 1995, "Purification and characterisation of a metallopeptidase of Candida albicans," J. Med. Microbiol, 43(4):282-288.

Embery et al., 1994, "Gingival Crevicular Fluid: Biomarkers of Periodontal Tissue Activity," Adv. Dent. Res. 8(2):329-336.

Fokkema et al., 2003, "Monocyte-derived RANTES is intrinsically elevated in periodontal disease while MCP-1 levels are related to inflammation and are inversely correlated with IL-12 levels," Clin. & Exp. Immunol. 131(3):477-483.

Fothergill et al., 1977, "Catabolism of L-Lysine by *Pseudomonas aureuginosa*," J. Gen. Micriobiol. 99(1):139-155.

Gallegos Olea Olea et al., 2002, "Organic Carbonate from *Caloptropis procera* Leaves," Fitoterapia 73(3):263-265.

Gaspersic et al., 2010, "Anti-NGF treatment reduces bone resorption in periodontitis," J. Dental Res. 89(5):515-520.

Golub et al., 1998, "Modulation of the Host Response in the Treatment of Periodontitis," Dent. Today 17(10):102-6. 108-9.

Golub et al., 1997, "A matrix metalloproteinase inhibitor reduces bone-type collagen degradation fragments and specific collagenases in gingival crevicular fluid during adult periodontitis," Inflamm. Res. 46:310-319.

Harrison, 2004, "Physiological Roles of Xanthine Oxidoreductase," Drug Metab. Rev. 36(2):363-375.

Heasman et al., 1993, "Changes in Crevicular Fluid Levels of Interleukin-1 Beta, Leukotriene B4, Prostaglandin E2, Thromboxane B2 and Tumour Necrosis Factor Alpha in Experimental Gingivitis in Humans," J. Periodontal Res. 28(4):241-247.

Holt et al., 2001, "Dental damage, sequelae, and prevention," Western J. of Medicine 174(4):288-290.

Ilgenli et al., 2006, "Gingival Crevicular Fluid Matrix Metalloproteinase-13 Levels and Molecular Forms in Various Types of Periodontal Diseases," Oral Dis. 12(6):573-579.

Imbert et al., 2002, "Effect of matrix metalloprotease inhibitors on the 95 kDa metallopeptidase of Candida albicans," J. Antibicrob. Chemother. 49(6):1007-1010.

Ingman et al., 1996, "Matrix metalloproteinases and their inhibitors in gingival crevicular fluid and saliva of periodontitis patients," J. Clin. Periodontal. 23(12):1127-1132.

Ingman et al., 1994, "Multiple Forms of Gelatinase/Type IV Collagenases in Saliva and Gingival Crevicular Fluid of Periodontitis Patients," J. Clin. Periodontol. 21(1):26-31.

International Search Report and Written Opinion in International Application No. PCT/US10/029674 mailed Nov. 12, 2010.

International Search Report and Written Opinion in International Application No. PCT/US10/029670 mailed Aug. 12, 2010.

International Search Report and Written Opinion in International Application No. PCT/US09/039184 mailed Jun. 25, 2010.

International Search Report and Written Opinion in international Application No. PCT/US09/039140 mailed Nov. 27, 2009.

International Search Report and Written Opinion in International Application No. PCT/US07/060222 mailed Aug. 2, 2007.

Ishikura et al., 2003, "Cloning of the Tannerella Forsythensis (Bacteriodes Forsythus) siaH1 Gene and Purification of the Sialidase Enzyme," J. Med. Micriobiol. 52(Pt. 12):1101-1107.

Jackson et al., 2007, "The Production of Reactive Oxygen and Nitrogen Species by Skeletal Muscle," J. Appl. Physiol. 102(4);1664-1670.

Jahngen et al., 1984, "High-Performance Liquid Chromatography Analysis of Purine Nucleosides in Human Gingival Crevicular Fluid," Arch. Oral Biol. 29(8):607-610.

Kantarci et al., 2003, "Neutrophil-Mediated Tissue Injury in Periodontal Disease Pathogenesis: Findings from Localized Aggressive Periodontitis," J. Periodontol. 74(1):66-75.

Karthikeyan et al., 2007, "Gingival Crevicular Fluid and Serum Leptin: Their Relationship to Periodontal Health and Disease," J. Clin. Periodontol. 34(6):467-472.

Kiili et al., 2002, "Collagenase-2 (MMP-8) and collagenase-3 (MMP-13) in adult periodontitis: molecular forms and levels in gingival crevicular fluid and immunolocalisation in gingival tissue," J. Clin. Periodontol. 29(3):224-232; Erratum in: J. Clin. Periodontol. 2004, 31(2):149.

Lamster et al., 2007, "Analysis of Gingival Crevicular Fluid As Applied to the Diagnosis of Oral and Systemic Diseases," Ann. NY Acad. Sci. 1098:216-229.

Lamster, 1997, "Evaluation of Components of Gingival Crevicular Fluid As Diagnostic Tests," Ann. Periodontol. 2(1):123-137.

Lamster et al., 1987, "The Polyamines Putrescine, Spermidine and Spermine in Human Gingival Crevicular Fluid," Arch. Oral Biol. 32(5):329-333.

Lapp et al., 2005, "Analysis of interleukin-activated human gingival fibroblasts; modulation of chemokine responses by female hormones," J. Periodontol. 76(5);803-812.

Lawton et al., 2008, "Analysis of the Adult Human Plasma Metabolome," Pharmacogenomics 9(4):383-397.

Loos et al., 2005, "Host-Derived Diagnostic Markers for Periodontitis: Do They Exist in Gingival Crevice Fluid?" Periodontol. 39:53-72.

Lorencini et al., 2009, "Changes in MMPs and inflammatory cells in experimental gingivitis," Histol. Histopathol. 24(2):157-166.

Madianos et al., 2005, "Generation of inflammatory stimuli: how bacteria set up inflammatory responses in the gingiva," J. Clin. Periodontol. 32(Supp. 6):57-71.

Mahanonda et al., 2002, "Upregulation of co-stimulatory molecule expression and dendritic cell marker (CD83) on B cells in periodontal disease," J. Periodontal Res. 37(3):177-183.

Mantyla et al., 2003, "Gingival crevicular fluid collagenase-2 (MMP-8) test stick for chair-side monitoring of periodontitis," J. Periodontol. Res. 18(4):436-439.

McAllister et al., 2008, "Spit Tests: Searching for Biomarkers in the Salivary Proteome," Poster 37, 8th European Symposium on Saliva, May 14-17, 2008, The Netherlands.

Modeer et al., 1996, "Triclosan reduces prostaglandin biosynthesis in human gingival fibroblasts challenged with interleukin-1 in vitro," J. Clin. Periodontol. 23(10):927-933.

Morisseau et al., 1999, "Potent Urea and Carbamate Inhibitors of Solble Epoxide Hydrolases," PNAS 96(16):8849-8854.

Nixon et al., 2000, "Cytokine responses to *Treponema pectinovorum* and *Treponema denticola* in human gingival fibroblasts," Infect. & Immun. 68(9):5284-5292.

Ogawa et al., 2002, "Cell activation by *Porphyromonas gingivalis* lipid A molecule through Toll-like receptor 4- and myeloid differentiation factor 88-dependent signaling pathway," Int. Immunol. 14(11):1325-1332.

Ozmeric, 2004, "Advances in Periodontal Disease Markers," Clin. Chim. Acta 343(1-2):1-16.

Pacher et al., 2006, "Therapeutic Effects of Xanthine Oxidases inhibitors: Renaissance Half a Century after the Discovery of Allopurinol," Pharmacol. Rev. 58(1):87-114.

Page et al., 1991, "The role of inflammatory mediators in the pathogenesis of periodontal disease," J. Periodontol. Res. 26(3 Pt. 2):230-242.

Pihlstrom et al., 2005, "Periodontal Diseases," Lancet 366(9499):1809-1820.

Pozo et al., 2005, "Longitudinal analysis of metalloproteinases, tissue inhibitors of metalloproteinases and clinical parameters in gingival crevicular fluid from periodontitis-affected patients," J. Periodontol. Res. 40(3):199-207.

Pradeep et al., 2007, "Gingival Crevicular Fluid Levels of Neopterin in Healthy Subjects and in Patients with Different Periodontal Diseases," J. Periodontol. 78(10):1962-1967.

Prapulla et al., 2007, "Gingival Crevicular Fluid VEGF Levels in Periodontal Health and Disease," J. Periodontol. 78(9): 1783-1787.

Preshaw et al., 2004, "Subantimicrobial dose doxycycline as adjunctive treatment for periodontitis. A review," J. Clin. Periodontol. 31(9):697-707.

Putnin et al., 2002, "Induction of keratinocyte growth factor 1 Expression by lipopolysaccharide is regulated by CD-14 and toll-like receptors 2 and 4," Infect. & Immun. 70(12):6541-6548.

(56) References Cited

OTHER PUBLICATIONS

Qin et al., 2006, "Effect of Minocycline Hydrochloride Ointment on IL-8 in Gingival Crevicular Fluid," Wuhan Daxue Xuebao [Medical Journal of Wuhan University] 27(1):75-78, english abstract.
Romer et al., 1999. "A *Candida albicans* metallopeptidase degrades constitutive proteins of extracellular matrix," FEMS Microbiol. Lett. 177(2):205-210.
Rossomando et al., 1993, "A novel method for the detection of TNF-alpha in gingival crevicular fluid," J. Periodontol. 64(5 Suppl):445-449.
Ruwanpura et al., 2004, "Prostaglandin E2 regulates interleukin-1beta-induced matrix metalloproteinase-3 production in human gingival fibroblasts," J. Dental Res. 83(3):260-265.
Search Report from the European Patent Office for Corresponding European Patent Application No. EP 1015338 dated Aug. 3, 2010.
Segal et al., 2000, "Xanthine Oxidase Contributes to Host Defense against *Burkhoideria cepacia* in the p47(phox−/−) Mouse Model of Chronic Granulomatous Disease," Infect. Immun. 68(4):2374-2378.
Seymour et al., 2007, "Relationship between Periodontal Infections and Systemic Disease," Clin. Microbiol. Infect. 13(Suppl. 4):3-10.
Smalley, 1994, "Pathogenic Mechanisms in Periodontal Disease," Adv. Dent. Res. 8(2):320-328.
Sorsa et al., 1990, "The role of gingival crevicular fluid and salivary interstitial collagenases in human periodontal diseases," Arch. Oral Biol. 35 Suppl:193S-196S.
Stevens et al., 2000, "Antibacterial Properties of Xanthine Oxidase in Human Milk," Lancet 356(9232):829-830.
Sugawara, 2003, "Host Defense Mechanisms in Oral Mucosa," Tohoku University Dental Journal 22:11-18, english abstrct.
Sugawara et al., 2002, "Innate immune responses in oral mucosa," J. Endotoxin Res. 8(6):465-468.
Szasz et al., 2007, "A Comparison of Arteries and Veins in Oxidative Stress: Producers, Destroyers, Function, and Disease," Exp. Biol. Med. (Maywood) 232(1):27-37.
Taba et al., 2005: "Diaanostic Biomarkers for Oral and Periodontal Diseases," Dent. Clin. North Am. 49(3):551-571.
Tatakis et al., 2005, "Etiology and pathogenesis of periodontal diseases," Dent. Clin. N. Am. 49:491-516.
Teng et al., 1992, "Gingival crevicular fluid gelatinase and its relationship to periodontal disease in human subjects," J. Periodontal Res. 27(5):544-552.
Tervahartiala et al., 2000, "The in vivo Expression of the Collagenolytic Matrix Metalloproteinases (MMP-2 , -8, -13, and -14) and Matrilysin (MMP-7) in Adult and Localized Juvenile Periodontitis" J. Dental Res. 79(12):1969-1977.
Toker et al., 2006, "Effect of meloxicam on gingival crevicular fluid IL-1beta and IL1 receptor antagonist levels in subjects with chronic periodontitis, and its effects on clinical parameters," Clin. Oral Investig. 10(4):305-310.
Tsai et al., 2005, "Lipid Peroxidation: A Possible Role in the Induction and Progression of Chronic Periodontitis," J. Periodontal Res. 40(5):378-384.
Tu et al., 2009, "Cyclosporine A enhances apoptosis in gingival keratinocytes of rats and in OECMI cells via the mitochondrial pathway," J. Periodontal Res, 44(6):767-775.
Uehara et al., 2002, "Priming of human oral epithelial cells by interferon-gamma to secrete cytokines in response to lipopolysaccharides, lipoteichoic acids and peptidoglycans," J. Med. Microbiol. 51(8):626-634.
Uehara et al., 2001, "Contrasting responses of human gingival and colonic epithelial cells to lipopolysaccharides, lipoteichoic acids and peptidoglycans in the presence of soluble CD14," Med. Microbiol. Immunol. 189(4):185-192.
Valko et al., 2007, "Free Radicals and Antioxidants in Normal Physiological Functions and Human Disease," Int. J. Biochem. Cell Biol. 39(1):44-84.
Van Dyke et al., 2003, "Resolution of inflammation: A New Paradigm for the Pathogenesis of Periodontal Diseases," J. Dent. Res. 82(2):82-90.
Wang et al., 2002, "*Porphyromonas gingivalis* lipopolysaccharide signaling in gingival fibroblasts CD14 and Toll-like receptors," Crit. Rev. Oral Biol. Med. 13(2):132-142.
Weinberg et al., 1998, "Epithelial antimicrobial peptides: review and significance for oral applications," Crit. Rev. Oral Biol. Med. 9(4):399-414.
Xu et al., 2004, "Effectiveness of a Triclosan/Copolymer Dentifrice on Microbiological and Inflammatory Parameters," Compend. Contin. Educ. Dent., Medline Database Accession No. NLM15645886.
Yang et al., 2006, "Eukaryotic Pathways for the Induction of Peptidase by Pathogenic Oral Bacteria," D-144, http://ieg.ou.edu/ASM2006/data/papers/D_144.htm.
Yoshimura, 2004, "Recognition of Periodontopathic Bacteria by Innate Immune System," J. Japanese Soc. Of Periodontol. 46:94-100.
Yoshioka et al., 2003, "Effect of hydroxamic acid-based matrix metalloproteinase inhibitors on human gingival cells and *Porphyromonas gingivalis*," J. Periodontol. 74(8):1219-1224.
Borovsky et al., 2004, Therapeutic Stomatology, Textbook for students of medical institutes/edited by E.V. Borovsky, Chapter 5 (151-156); Chapter 6 (527-529); Chapter 12 (10-13).
Panagakos et al., Jun. 25-28, 2003, "2248 Triclosan Inhibition of Cytokine-stimulated MMP Production by Osteoblast-like Cells", 81st General Session of the International Association for Dental Research—Seq. #227—Biologic Response Modifiers and Tissue Formation, Retrieved from the Internet at <Url: http://iadr.confex.com/iadr/2003Goteborg/techprogram/abstract_33991.htm>.

ANTI BONE-LOSS AND ANTI ATTACHMENT-LOSS EFFECTS OF AN ORAL COMPOSITION

CROSS-REFERENCE TO RELATED APPLICATIONS

The present application is a national stage entry under 35 U.S.C.§371 of International Patent Application No. PCT/US2010/029670, filed Apr. 1, 2010, which claims priority to U.S. Provisional Application No. 61/165,685, filed Apr. 1, 2009, the entireties of which are hereby incorporated by reference.

BACKGROUND

Periodontitis is characterized, in part, by abnormal and excessive degradation of the periodontal organic matrix. This matrix includes the gingiva, periodontal ligament, cementum and alveolar bone. At least a portion of the destruction of the matrix is mediated by the overproduction of matrix metalloproteinases (MMPs), a family of zinc-dependent endopeptidases. MMPs also facilitate bone resorption by degrading the osteoid (i.e., the non-mineralized and newly-synthesized bone matrix), then degrading the matrix. These events result in the clinical manifestation of periodontitis, including gingival recession, pocket formation, loss of attachment, and eventual tooth loss.

SUMMARY

The invention includes a method for treating periodontitis in a mammal in need thereof comprising contacting a cell in the mouth of the mammal with an agent that down-regulates at least one matrix metalloproteinase selected from the group consisting of MMP-9 and MMP-13, wherein the down-regulation of the metalloproteinase correlates with a reduction in at least one symptom associated with periodontitis.

The invention also includes a method of identifying a compound useful in treating periodontitis in a mammal, the method comprising contacting a cell with a test compound and determining whether the test compound down-regulates at least one matrix metalloproteinase selected from the group consisting of MMP-9 and MMP-13, wherein the down-regulation of at least one of the matrix metalloproteinases is an indication that the test compound is useful to treat periodontitis.

The invention also includes a method of treating periodontitis in a mammal in need thereof comprising administering to the oral cavity of the mammal an oral composition comprising 2,4,4'-trichloro-2'-hydroxydiphenyl ether in an amount which is effective to down-regulate at least one matrix metalloproteinase in the oral cavity of the mammal, the matrix metalloproteinase being selected from the group consisting of MMP-9 and MMP-13, wherein the down-regulation of the matrix metalloproteinase results in the treatment of periodontitis in the mammal.

The invention further includes a method of reducing a pathological excess of matrix metalloproteinase activity in the oral cavity of a mammal in need thereof comprising administering to the oral cavity of the mammal an oral composition comprising 2,4,4'-trichloro-2'-hydroxydiphenyl ether in an amount which is effective for reducing the matrix metalloproteinase activity in the oral cavity of the mammal, the matrix metalloproteinase being selected from the group consisting of MMP-9 and MMP-13, wherein the inhibition of the matrix metalloproteinase activity results in the inhibition of an excessive degradation of connective tissue matrix protein components.

The invention includes a method of reducing a pathological excess of matrix metalloproteinase in the oral cavity of a mammal in need thereof comprising administering to the oral cavity of the mammal an oral composition comprising 2,4,4'-trichloro-2'-hydroxydiphenyl ether in an amount which is effective for reducing the matrix metalloproteinase level in the oral cavity of the mammal, wherein the inhibition of the matrix metalloproteinase level results in the inhibition of an excessive degradation of connective tissue matrix protein components, and wherein the matrix metalloproteinase is selected from the group consisting of MMP-9 and MMP-13.

In an embodiment, a method includes an oral composition comprising 0-36% by weight of a siliceous polishing agent; 0.25%-0.35% by weight of a substantially water insoluble noncationic antibacterial agent selected from the group consisting of halogenated diphenyl ethers, halogenated salicylanilides, benxoic esters, halogenated carbanilides and phenolic compounds; and an effective amount of 0.01%-4.0% by weight of an antibacterial-enhancing agent which enhances delivery and adherence of said antibacterial agent to, and the retention thereof on, oral tooth and gum surfaces, wherein said antibacterial-enhancing agent is (i) a copolymer of maleic acid or anhydride with another inert ethylenically unsaturated polymerizable monomer or (ii) poly (beta-styrene-phosphonic acid) or poly (alpha-styrenephosphonic acid) polymer or a copolymer of either styrenephosphonic acid with another ethylenically unsaturated monomer, and the composition optionally further comprising an amount of a fluoride ion-providing source sufficient to supply 25 ppm to 5,000 ppm of fluoride ions. In an embodiment, an oral composition comprises 0.01-36% by weight of a siliceous polishing agent. In another embodiment, an oral composition does not comprise a siliceous polishing agent.

In an embodiment, a method includes an oral composition comprising an effective anticalculus amount of at least one water-soluble linear molecularly-dehydrated polyphosphate salt as an essential anticalculus agent, an effective antiplaque amount of a substantially water insoluble noncationic antibacterial compound as an essential antiplaque agent, and, optionally, an amount of a fluoride ion-providing source sufficient to supply 25 ppm to 5,000 ppm of fluoride ions. In an aspect, 2,4,4'-trichloro-2'-hydroxydiphenyl ether is present in a composition at a concentration from 1 ppm to 100 ppm.

In an embodiment, an oral composition is a mouthwash or a mouthrinse. In an aspect, a mouthwash or mouthrinse does not comprise a siliceous polishing agent.

DETAILED DESCRIPTION

Three major destructive MMPs in periodontitis are MMP-8, MMP-9, and MMP-13. MMP-8 and MMP-13 are collagenases, and MMP-9 is a gelatinase. All three enzymes can be found in diseased periodontal tissue and gingival crevicular fluid. The levels of these enzymes are positively correlated to periodontitis clinical indices. That is, elevated, or "above normal" levels of at least one of MMP-8, MMP-9, and MMP-13 is an indication of periodontits. The measurements may be made of MMP-8. MMP-9, and MMP-13 enzymes, RNA, or biological activity.

As set forth herein, it is now shown that an oral composition comprising 2,4,4'-trichloro-2'-hydroxydiphenyl ether (triclosan) can be used to reduce the levels of at least one of MMP-8, MMP-9, and MMP-13 in the oral cavity of a mammal. In an embodiment, the oral composition is a dentifrice. In another embodiment, the oral composition comprises a mouthwash, a patch, or a gel, among other things. In another aspect, an antibacterial compound can be used to reduce the levels of at least one of MMP-8, MMP-9, and MMP-13 in the oral cavity of a mammal.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

As used herein, the term "periodontitis" refers to abnormal and excessive degradation of the periodontal organic matrix, including the gingiva, periodontal ligament, cementum and alveolar bone. The clinical manifestation of periodontitis includes, but is not limited to, gingival recession, pocket formation, loss of matrix attachment, tooth and bone loss. Periodontitis may be characterized as early periodontitis, moderate periodontitis or advanced periodontitis. However, periodontitis should not be limited to only those symptoms and sequelae set forth herein, as will be understood by the skilled artisan. Early periodontitis is clinically manifested, among other symptoms, by one or more of: bleeding upon probing; the presence of pockets (3 to 4 mm); localized areas of recession; attachment loss (3 to 4 mm); bone loss (e.g., horizontal); and class I furcation invasion areas. Moderate periodontitis is clinically manifested, among other symptoms, by one or more of: the presence of pockets (4 to 6 mm); the presence of attachment loss (4 to 6 mm); bleeding upon probing; grade I and/or grade II furcation invasion areas; class I tooth mobility; bone loss (e.g., horizontal and/or vertical); and loss of ⅓ of supporting alveolar bone (i.e., crown to root ratio of 1:1). Advanced periodontitis is clinically manifested by one or more of: bleeding upon probing; the presence of pockets (over 6 mm); attachment loss (over 6 mm); grade II and/or grade III furcation invasion areas; class II and/or class III tooth mobility; bone loss (e.g., horizontal and/or vertical); and loss of over ⅓ of supporting alveolar bone (i.e., crown to root ratio of 2:1 or more). Periodontitis is divided into subdivisions including, but not limited to: adult periodontitis (e.g., plaque-associated); early-onset periodontitis (e.g., prepubertal, juvenile, rapidly progressive and the like); periodontitis associated with systemic diseases; necrotizing ulcerative periodontitis; refractory periodontitis; peri-implantitis and the like.

The term "treating", as used herein, refers to a detectable improvement in an adverse condition and/or a lessening the symptoms of the condition upon contacting a mammal with an oral composition of the invention and/or according to a method of the invention.

The term "treatment of periodontitis" will be understood to include the prevention of periodontitis in a mammal, as well as inhibition of the progression of one or more pre-existing conditions associated with periodontitis in a mammal. As used herein, the terms "inhibit" and "inhibition" refer to a partial inhibition or a complete inhibition of periodontitis compared to the condition without treatment, such that therapeutic treatment and/or prophylaxis results. Treatment of periodontitis according to the invention therefore includes the reduction, inhibition of, improvement of, lessening, diminishment, cessation, or elimination of one or more of the symptoms and/or sequelae set forth herein.

As used herein, "pathological excess" refers to activity above an accepted normal level. For example, a "pathological excess" of matrix metalloproteinase activity is a level of matrix metalloproteinase activity that is above the level normally found in a non-disease state. As used herein, a "pathological excess of matrix metalloproteinase activity" is a level of matrix metalloproteinase activity associated with periodontitis.

As used herein, the term "down regulate" refers to a decrease in enzymatic activity, a decrease in the level of enzymatic activity, a decrease in the level of protein and/or nucleic acid encoding such protein, or a decrease in the biochemical effect of the presence of a protein, such as one or more of MMP-8, MMP-9, and MMP-13.

In an aspect, the invention provides a method of reducing a pathological excess of at least one of MMP-8, MMP-9 and MMP-13 in the oral cavity of a mammal in need thereof comprising administering to the oral cavity of the mammal an oral composition comprising 2,4,4'-trichloro-2'-hydroxydiphenyl ether in an amount which is effective for reducing the matrix metalloproteinase level in the oral cavity of the mammal, wherein the inhibition of the matrix metalloproteinase level results in the inhibition of an excessive degradation of connective tissue matrix protein components.

An MMP, such as MMP-8, MMP-9 or MMP-13, may be reduced in the oral cavity in one of multiple ways, as set forth herein. In an embodiment, an MMP may be reduced in the oral cavity by down-regulating the MMP at the nucleic acid level, as set forth elsewhere herein. Such a reduction may result in a reduction in one or more of the nucleic acid encoding the MMP (e.g., mRNA) and the MMP enzyme expressed into the oral cavity. Reduction of the mRNA encoding an MMP, for example, may be effected by one or more of multiple techniques, as will be understood by the skilled artisan, when armed with the disclosure set forth herein. Examples include reducing the transcription of mRNA encoding the MMP and degradation/elimination of the mRNA encoding the MMP.

In another embodiment, an MMP may be reduced in the oral cavity by directly reducing the amount of MMP enzyme. Reduction of MMP enzyme may be effected by one or more of multiple techniques, as will be understood by the skilled artisan, when armed with the disclosure set forth herein. Examples include inhibition of the enzyme via a small molecule inhibitor, inhibition via a natural or biologically-derived molecule, proteolytic degradation of the enzyme, and affinity-based clearance of the enzyme from the oral cavity, among others. An agent that reduces one or more of MMP-8, MMP-9 or MMP-13 may be an agent as described herein, such as 2,4,4'-trichloro-2'-hydroxydiphenyl ether (TRICLOSAN), or it may be another antibacterial agent. In another aspect, an agent may be something other than an antibacterial agent. As such, the invention provides methods of treating an individual afflicted with periodontitis.

In an aspect of the invention, a method is provided for reducing a pathological excess of matrix metalloproteinase activity in the oral cavity of a mammal in need thereof comprising administering to the oral cavity of the mammal an oral composition comprising 2,4,4'-trichloro-2'-hydroxydiphenyl ether in an amount which is effective for reducing the matrix metalloproteinase activity of at least one of MMP-8, MMP-9 and MMP-13 in the oral cavity of the mammal, wherein the inhibition of the matrix metalloproteinase activity results in the inhibition of an excessive degradation of connective tissue matrix protein components. In another aspect, administering to the oral cavity of the mammal an oral composition comprising 2,4,4'-trichloro-2'-hydroxydiphenyl ether is done in an amount which is effective for reducing the level of at least one of MMP-8, MMP-9 and MMP-13 in the oral cavity of the mammal, wherein the reduction of the level of the matrix metalloproteinase results in an reduction in the overall enzymatic activity of the metalloproteinase, resulting in the inhibition of excessive degradation of connective tissue matrix protein components. In an embodiment, a pathological excess of one or more MMPs may be reduced as described elsewhere herein with respect to reduction in the amount of MMP in the oral cavity of a mammal. That is, an MMP may be reduced at one or both of the nucleic acid and protein levels. As described elsewhere herein, the reduction in a pathological excess of one or more such MMP's can provide treatment of periodontitis in a mammal.

In another aspect, the invention provides a method of reducing the activity of at least one of MMP-8, MMP-9 and MMP-13 in the oral cavity of a mammal in need thereof, comprising administering to the oral cavity of the mammal an oral composition comprising 2,4,4'-trichloro-2'-hydroxydiphenyl ether in an amount which is effective for reducing the matrix metalloproteinase level in the oral cavity of the mammal, wherein the inhibition of the matrix metalloproteinase level results in the inhibition of an excessive degradation of connective tissue matrix protein components. In an embodiment, the activity of one or more MMPs may be reduced as described elsewhere herein with respect to reduction in the amount of MMP protein in the oral cavity of a mammal. That is, an MMP may be reduced at one or both of the nucleic acid and protein levels, thereby reducing the activity of the MMPs in the oral cavity, either by directly reducing the activity of the MMP or indirectly, by reducing the level of MMP protein and/or nucleic acid.

In another aspect, the invention provides methods of treating periodontitis in a mammal in need thereof comprising contacting a cell in the oral cavity of the mammal with an agent that down-regulates one or both of at least one of MMP-8, MMP-9 and MMP-13. According to the invention, the down-regulation of the metalloproteinase correlates with a reduction in at least one symptom associated with periodontitis.

An MMP, such as MMP-8, MMP-9 or MMP-13, may be down-regulated at the nucleic acid level. By way of a non-limiting example, an MMP may be down-regulated according to the invention by down-regulating the mRNA encoding the MMP. In an embodiment, a method of the invention comprises contacting the oral cavity of a mammal with an agent that down-regulates one or more of MMP-8, MMP-9 or MMP-13. An agent that down-regulates one or more of MMP-8, MMP-9 or MMP-13 may be an agent as described herein, such as TRICLOSAN, or it may be another antibacterial agent. In another aspect, an agent may be something other than an antibacterial agent. As such, the invention provides methods of treating an individual afflicted with periodontitis.

In another aspect, the invention provides a method of treating periodontitis in a mammal in need thereof. In an embodiment, a method of treating periodontitis in a mammal in need thereof comprises administering to the oral cavity of the mammal an oral composition comprising 2,4,4'-trichloro-2'-hydroxydiphenyl ether in an amount which is effective to down-regulate at least one of MMP-8, MMP-9 and MMP-13, wherein the down-regulation of matrix metalloproteinase results in the treatment of periodontitis in the mammal. In another embodiment, a method of treating periodontitis in a mammal in need thereof comprises administering to the oral cavity of the mammal an oral composition comprising 2,4,4'-trichloro-2'-hydroxydiphenyl ether in an amount which is effective to reduce the level of at least one of MMP-8, MMP-9 and MMP-13, wherein the reduction in the level of matrix metalloproteinase results in the treatment of periodontitis in the mammal. In yet another embodiment, a method of treating periodontitis in a mammal in need thereof comprises administering to the oral cavity of the mammal an oral composition comprising 2,4,4'-trichloro-2'-hydroxydiphenyl ether in an amount which is effective to reduce the level of activity of at least one of MMP-8, MMP-9 and MMP-13, wherein the reduction in the level of matrix metalloproteinase activity results in the treatment of periodontitis in the mammal.

In a method of treating periodontitis by administering to the oral cavity of the mammal an oral composition, the activity of one or more MMPs may be reduced as described elsewhere herein with respect to reduction in the amount of MMP in the oral cavity of a mammal. That is, an MMP may be reduced at one or both of the nucleic acid and protein levels, thereby reducing the activity of the MMPs in the oral cavity. Similarly, the down-regulation of an MMP or the reduction in the level of an MMP may be affected by action at either or both of the nucleic acid and protein levels, as described in detail elsewhere herein.

In another aspect, the invention provides a method of identifying a compound useful in treating periodontitis in a mammal in need thereof, comprising contacting a cell with a test compound and determining whether the test compound down-regulates one or both of at least one of MMP-8, MMP-9 and MMP-13. The down-regulation of at least one of the matrix metalloproteinases is an indication that the test compound is useful to treat periodontitis.

In one embodiment, a method of treating periodontitis comprises administering an agent identified by a screening assay described herein, or a combination of agents that inhibit one or more markers of periodontitis, wherein at least one of the agents is an agent identified by a screening assay described herein.

In an embodiment, the invention provides a method for treatment of periodontitis, comprising the step of administering a therapeutically effective amount of an agent which inhibits the periodontal disease and/or periodontal disorder to a subject in need of such treatment. As defined herein, a therapeutically effective amount of agent (i.e., an effective dosage) ranges from 0.001 to 30 mg/kg body weight, preferably 0.01 to 25 mg/kg body weight, more preferably 0.1 to 20 mg/kg body weight, and even more preferably 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an inhibitor can include a single treatment or, preferably, can include a series of treatments. It will also be appreciated that the effective dosage of in used for treatment may increase or decrease over the course of a particular treatment. Changes in dosage may result from the results of diagnostic assays as described herein.

The skilled artisan will understand how to detect the presence of periodontitis. Additionally, the skilled artisan will understand how to identify an elevated level of one or more of MMP-8, MMP-9, and MMP-13. An exemplary method for detecting the presence or absence of periodontitis in a mammal comprises obtaining a biological sample from the oral cavity of a test subject and contacting the biological sample with a compound or an agent capable of detecting one or more of the markers of periodontitis (i.e. MMP-8, MMP-9, or MMP-13) described herein, e.g., marker nucleic acid (e.g., mRNA, genomic DNA, among others) or marker peptide (e.g., peptide fragment or protein, among others) encoded by the marker nucleic acid such that the presence of a marker nucleic acid or marker peptide encoded by the nucleic acid is detected in the biological sample. In an embodiment, an agent for detecting marker mRNA or genomic DNA is a labeled nucleic acid probe capable of hybridizing to marker mRNA or genomic DNA. The nucleic acid probe can be, for example, a full-length marker nucleic acid or a portion thereof. Other suitable probes for use in the diagnostic assays of the invention are described herein. In another embodiment, the activity of a marker of periodontitis is used as a way to detect the marker (i.e. MMP-8, MMP-9, or MMP-13 activity). Any assay now known or later developed to detect the activity of a marker is encompassed herein.

In another embodiment, an agent for detecting marker peptide is an antibody capable of binding to a marker peptide, such as an antibody with a detectable label. Antibodies can be polyclonal or monoclonal. An intact antibody, or a fragment thereof (e.g., Fab or F(ab').sub.2) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

As the term is used herein, "biological sample" is intended to include tissues, cells and biological fluids isolated from the oral cavity of a subject, as well as tissues, cells and fluids present within the oral cavity of a subject. That is, the detection method of the invention can be used to detect marker mRNA, peptide (e.g., protein), or genomic DNA in a biological sample in vitro as well as in vivo. By way of a non-limiting example, in vitro techniques for detection of marker mRNA include Northern hybridizations and in situ hybridizations. In vitro techniques for detection of marker peptide include enzyme linked immunosorbent assays (ELISAs), Western blots, immunoprecipitations and immunofluorescence. In vitro techniques for detection of marker genomic DNA include Southern hybridizations. In vivo techniques for detection of marker peptide include introducing into the oral cavity of a subject a labeled anti-marker antibody. For example, the antibody can be labeled with a radioactive marker whose presence and location in a subject can be detected by standard imaging techniques.

In an embodiment, the methods further involve obtaining a control biological sample from a control subject, contacting the control sample with a compound or agent capable of detecting marker peptides, mRNA, or genomic DNA, such that the presence of marker peptide, mRNA or genomic DNA is detected in the biological sample, and comparing the presence of marker peptides, mRNA or genomic DNA in the control sample with the presence of marker peptide, mRNA or genomic DNA in the test sample. Alternatively, the presence of marker peptide, mRNA or genomic DNA in the test sample can be compared with information in a database or on a chart to result in detection or diagnosis. In another embodiment, the methods further involve using a control biological sample obtained from the subject having periodontitis, wherein the control sample was obtained from the subject prior to the onset of periodontitis (i.e., when the subject was healthy or in a "normal", non-periodontitis state).

By way of a non-limiting example, the level of MMP-9 may be ascertained in vitro by contacting a cell with TNFα. In an embodiment, a cell is a monocyte. After contacting a cell with TNFα, the level of MMP-9 is detected at either the protein or nucleic acid level. In an aspect, the level of MMP-9 is also ascertained in vitro by contacting a cell with TNFα in the presence of an antibacterial agent. In an embodiment, the antibacterial agent is 2,4,4'-trichloro-2'-hydroxydiphenyl ether. In another embodiment, and agent is doxycycline. In another aspect, an agent may be something other than an antibacterial agent. In an embodiment, an agent is an MMP inhibitor.

In an embodiment of the invention, a measure of down-regulation of MMP-9 by detecting the level of MMP-9 is ascertained in vitro by contacting a cell with TNFα in the presence of an agent, such as an antibacterial agent and comparing the level of MMP-9 ascertained in vitro by contacting a cell with TNFα in the absence of an antibacterial agent, wherein the experimental conditions are otherwise identical. A lower level of MMP-9 protein, nucleic acid or enzymatic activity in the presence of antibacterial agent than in the absence of antibacterial agent is an indication that the antibacterial compound down-regulates MMP-9. Based on the disclosure set forth herein, it will be understood that the same methods may be used to evaluate MMP-8 and/or MMP-13.

It will be understood that an in vitro measure of down regulation of MMP-8, MMP-9 and/or MMP-13 can be correlated to an in vivo effect, observation or result. In an aspect, down regulation of a metalloproteinase measured in vitro is a confirmation of an in vivo observation, including, but not limited to, treatment of periodontitis, a method of reducing a pathological excess of metalloproteinase and/or metalloproteinase activity in vivo, and a method of identifying a compound useful to treat periodontitis and/or reduce a pathological excess of metalloproteinase and/or metalloproteinase activity in vivo. See, for example, Golub et al., Inflamm. Res. (1997) 46:310-9, Preshaw et al., J. Clin. Periodontol. (2004) 31:697-707; Mantyla et al., J. Periodontal. Res. (2003) 38:436-439; Lorencini et al., Histol. Histopathol. (2009) 24:157-166; and Pozo et al., J. Periodontal Res. (2005) 40:199-207. In another aspect, down regulation of a metalloproteinase measured in vitro is a predictor of an in vivo result, including, but not limited to, treatment of periodontitis, a method of reducing a pathological excess of metalloproteinase and/or metalloproteinase activity in vivo, and a method of identifying a compound useful to treat periodontitis and/or reduce a pathological excess of metalloproteinase and/or metalloproteinase activity in vivo.

By way of another non-limiting example, the level of MMP-13 may be ascertained in vitro by contacting a cell with parathyroid hormone (PTH). In an embodiment, a cell is an osteoblast. After contacting a cell with PTH, the level of MMP-13 is detected at either the protein or nucleic acid level. In an aspect, the level of MMP-13 is also ascertained in vitro by contacting a cell with PTH in the presence of an antibacterial agent. In an embodiment, the antibacterial agent is 2,4,4'-trichloro-2'-hydroxydiphenyl ether. A lower level of MMP-13 protein, nucleic acid or enzymatic activity in the presence of antibacterial agent than in the absence of antibacterial agent is an indication that the antibacterial compound down-regulates MMP-13.

In an aspect, the ability of an oral composition as set forth herein to treat periodontitis is ascertained by comparison of the effect of 2,4,4'-trichloro-2'-hydroxydiphenyl ether on metalloproteinase down regulation with the effect of the oral composition on metalloproteinase down regulation. In another aspect, the ability of any oral composition to treat periodontitis is ascertained by comparison of the effect of the oral composition, either in vivo or in vitro, with the effect of an oral composition as set forth herein.

The invention further includes an oral composition, such as a dentifrice, gel, patch, mouthwash, or spray, among others, for use in a method of the invention. In an aspect, an oral composition comprises an antibacterial agent. In an exemplary embodiment, the antibacterial agent is a noncationic antibacterial agent. See, for example, U.S. Pat. No. 5,288,480, which is hereby incorporated by reference in its entirety herein. The noncationic antibacterial agent is present in the oral composition in an effective antiplaque amount of 0.25-0.35% by weight, preferably 0.3%. The antibacterial agent is substantially water-insoluble, meaning that its solubility is less than 1% by weight in water at 25° C. and may be even less than 0.1%. When an oral composition is a mouthwash, for example, the concentration of antibacterial agent may be reduced up to 10-fold over that which is used in another dentifrice, such as a toothpaste. In an embodiment, the antibacterial agent is 2,4,4'-trichloro-2'-hydroxydiphenyl ether. In another embodiment, the oral composition comprises two or more antibacterial agents.

In an embodiment, an antibacterial-enhancing agent (AEA) enhances delivery of the antibacterial agent to, and retention thereof on oral surfaces. In an aspect, an AEA comprises an adherent material. See U.S. Pat. No. 5,288,480 for descriptions of materials and compositions useful for AEA materials of the present invention, as well as for general descriptions of oral compositions, such as dentifrice compositions, useful in the present invention. By way of a non-limiting example, an adherent material in a composition is a polymer having a number average molecular weight between 100,000 and 2,500,000, inclusive. In an aspect, the adherent material is selected from polymers of polyvinyl phosphonic acid, poly(1-phosphonopropene)sulfonic acid, poly(beta styrene phosphonic acid), alpha styrene phosphonic acid, synthetic anionic polymeric polycarboxylate, maleic anhydride, maleic acid, and methyl vinyl ether. In another aspect, the adherent molecule is a polymer of methyl vinyl ether and maleic anhydride. An antibacterial-enhancing agent can be used at a level that is 0.01%-4.0% by weight of an oral composition.

As used herein, a "delivery-enhancing group" refers to one which attaches or substantively, adhesively, cohesively or otherwise bonds the AEA (carrying the antibacterial agent) to oral (e.g. tooth and gum) surfaces, thereby "delivering" the antibacterial agent to such surfaces. The organic retention-enhancing group, generally hydrophobic, attaches or otherwise bonds the antibacterial agent to the AEA, thereby promoting retention of the antibacterial agent to the AEA and indirectly on the oral surfaces. In some instances, attachment of the antibacterial agent occurs through physical entrapment thereof by the AEA, especially when the AEA is a cross-linked polymer, the structure of which inherently provides increased sites for such entrapment. The presence of a higher molecular weight, more hydrophobic cross-linking moiety in the cross-linked polymer still further promotes the physical entrapment of the antibacterial agent to or by the cross-linked AEA polymer.

In an embodiment, an antibacterial-enhancing agent which enhances delivery and adherence of said antibacterial agent to, and the retention thereof on, oral tooth and gum surfaces is (i) a copolymer of maleic acid or anhydride with another inert ethylenically unsaturated polymerizable monomer or (ii) poly (beta-styrene-phosphonic acid) or poly (alpha-styrene-phosphonic acid) polymer or a copolymer of either styrene-phosphonic acid with another ethylenically unsaturated monomer. However, the skilled artisan will understand that the present invention is not limited by the specific antibacterial enhancing agent used, and that other antibacterial enhancing agents are encompassed by the present invention.

In an exemplary dentifrice, an orally acceptable vehicle including a water-phase with humectant is present. Water is present typically an amount of at least 3% by weight, generally 3-35% and humectant, preferably glycerine and/or sorbitol, typically total 6.5-75% or 80% by weight of the dentifrice, more typically 10-75%. Although not required in the present invention wherein 0-25-0.35% of the water insoluble non-cationic antibacterial agent is present optionally, an additional ingredient which assists solubilization of the antibacterial agent in saliva may be incorporated in the water-humectant vehicle. Such optional solubilizing agents include humectant polyols such as propylene glycol, dipropylene glycol, and hexylene glycol, cellosolves such as methyl cellosolve and ethyl cellosolve, vegetable oils and waxes containing at least 12 carbons in a straight chain such as olive oil, castor oil and petrolatum and esters such as amyl acetate, ethyl acetate and benzyl benzoate. As used herein "propylene glycol" includes 1,2-propylene glycol and 1,3-propylene glycol. Significant amounts of polyethylene glycol particularly of molecular weight of 600 or more should be avoided since polyethylene glycol effectively inhibits the antibacterial activity of the noncationic antibacterial agent. For instance, polyethylene glycol (PEG) 600 when present with triclosan in a weight ratio of 25 triclosan:1 PEG 600 reduces the antibacterial activity of triclosan by a factor of 10-20 from that prevailing in the absence of the polyethylene glycol.

The pH of an oral composition is generally in the range of 4.5 to 10 and in another aspect, 6.5 to 7.5. It is noteworthy that the compositions of the invention may be applied orally at a pH below 5 without substantially decalcifying or otherwise damaging dental enamel. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc.).

Any abrasive particulates may be used and may be selected from sodium bicarbonate, calcium phosphate (e.g., dicalcium phosphate dihydrate), calcium sulfate, precipitated calcium carbonate, silica (e.g., hydrated silica), iron oxide, aluminum oxide, perlite, plastic particles, e.g., polyethylene, and combinations thereof. In particular, the abrasive may be selected from a calcium phosphate (e.g., dicalcium phosphate dihydrate), calcium sulfate, precipitated calcium carbonate, silica (e.g., hydrated silica), calcium pyrophosphate and combinations. Any type of silica may be used, such as precipitated silicas or silica gels. Preferred are commercially available silicas such as INEOS AC43, available from Ineos Silicas, Warrington, United Kingdom. Other abrasives may also be used in accordance with the present invention. As set forth in U.S. Pat. No. 4,358,437, powdered forms of calcium carbonate in an abrasive form constitute one important class of such abrasives. Examples of these abrasives are milled limestone or marble, chalks such as aragonite, calcite or mixtures thereof, and synthetically precipitated chalks such as waterworks chalk. Generally, the calcium carbonate should have a weight median diameter of less than 40 microns, preferably less than 15 microns. A second class of abrasives are powdered silicas, particularly, silica xerogels as defined in U.S. Pat. No. 3,538,230.

In an embodiment, an oral composition comprises a siliceous polishing agent. The polishing agent may be a siliceous material such as a hydrous silica gel, a silica xerogel or a complex amorphous alkali metal aluminosilicate or zirconosilicate or a precipitated silica. Colloidal silica materials include those sold under the trademark SYLOID such as those which have been sold as SYLOID 72 and SYLOID 74. Precipitated silicas include those sold under the trademark ZEODENT such as ZEODENT 113 and ZEODENT 115 and ZEODENT 119.

A mouthwash or mouthrinse will generally not comprise an abrasive particulate or a polishing particulate. A patch will generally not comprise an abrasive particulate or a polishing particulate.

Without being bound to a theory whereby the advantages of this invention are achieved, it is believed that even in the absence of a special solubilizing material for an antibacterial agent (e.g., 2,4,4'-trichloro-2'-hydroxydiphenyl ether), when the amount of agent is 0.25%-0.35% by weight and a polycarboxylate is present, sufficient agent is present to effect the treatment of periodontitis by way of down-regulation of at least one of MMP-8, MMP-9 or MMP-13. This is equally applicable to other water-insoluble noncationic antibacterial agents herein described.

An oral composition (e.g., dentifrice) may also contain a source of fluoride ions, or fluorine-providing component, as anti-caries agent, in an amount sufficient to supply 25 ppm to 5,000 ppm of fluoride ions. These compounds may be slightly soluble in water or may be fully water-soluble. They are characterized by their ability to release fluoride ions in water and by substantial freedom from undesired reaction with other compounds of the oral preparation. Among these materials are inorganic fluoride salts, such as soluble alkali metal, alkaline earth metal salts, or example, sodium fluoride, potassium fluoride, ammonium fluoride, calcium fluoride, a copper fluoride such as cuprous fluoride, zinc fluoride, barium fluoride, sodium flourosilicate, ammonium flourosilicate, sodium fluorozirconate, ammonium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate (MFP) and mixtures thereof, are preferred. Typically, in the cases of alkali metal fluorides, this component is present in an amount up to 2% by weight, based on the weight of the preparation, and preferably in the range of 0.05% to 1%. In the case of sodium monofluorophosphate, the compound may be present in an amount of 0.1-3%, and in an embodiment, 0.7-0.8%.

In an aspect, a composition further comprises an agent selected from a stannous ion agent; a fluoride compound; sodium fluoride; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4-ethylpyridinium chloride (TDEPC); octenidine; delmopinol; octapinol; nisin; zinc ion agent; copper ion agent; essential oils; furanones; bacteriocins, ethyllauroyl arginate, extracts of magnolia, a metal ion source, arginine, arginine bicarbonate, honokiol, magonol, ursolic acid, ursic acid, morin, extract of sea buckthorn, a peroxide, an enzyme, a Camellia extract, a flavonoid, a flavan, halogenated diphenyl ether, creatine, and propolis.

Some embodiments of the present invention provide methods of identifying a compound useful for treating a disease or condition of the oral cavity, the method comprising: obtaining a first gingival sample from a mammal suffering from a disease or condition of the oral cavity; obtaining a second gingival sample from the oral cavity of said mammal; contacting said first sample with a test compound; contacting said second sample with a positive control, wherein said positive control is a compound known to down-regulate the expression of one or more matrix metalloproteinases; measuring the extent to which the expression of one or more of said matrix metalloproteinases is down-regulated by said test compound; measuring the extent to which the expression of one or more of said matrix metalloproteinases is down-regulated by said positive control; and comparing the extent to which the expression of one or more of said matrix metalloproteinases is down-regulated by said test compound, with the extent to which the expression of one or more of said matrix metalloproteinases is down-regulated by said positive control; wherein a test compound that down-regulates the expression of one or more of said matrix metalloproteinases to an equal or greater extent than said positive control, is a compound useful in treating a disease or condition of the oral cavity.

In other embodiments, the one or more matrix metalloproteinases are selected from the group consisting of: MMP-8, MMP-9, and MMP-13. In further embodiments, the positive control down-regulates the expression of MMP-8. MMP-9, and MMP-13.

In some embodiments, the disease or condition of the oral cavity is gingivitis or periodontitis. In other embodiments, the positive control is a halogenated diphenylether. In yet other embodiments, the positive control is triclosan.

In some embodiments, the test compound down-regulates the expression of one or more of said matrix metalloproteinases to a greater extent than said positive control. In further embodiments, the test compound down-regulates the expression of MMP-9, and MMP-13, to a greater extent than said positive control. Still further embodiments provide methods wherein the test compound down-regulates the expression of MMP-8, MMP-9, and MMP-13, to a greater extent than the positive control.

In some embodiments, the positive control down-regulates the expression of MMP-8. In some embodiments, the positive control down-regulates the expression of MMP-9. In yet other embodiments, the positive control down-regulates the expression of MMP-13.

The invention is further described in the following examples. The examples are merely illustrative and do not in any way limit the scope of the invention as described and claimed.

EXAMPLES

Example 1

MMP-9 Preparation and Characterization

U937 cells and RPMI 1640 culture medium were obtained from ATCC. Human MMP-9 ELISA Kit (QUANTIKINE) was obtained from R&D Systems. Fetal Bovine Serum (FBS) was obtained from VWR, and the penicillin-streptomycin solution and Tumor Necrosis Factor $\alpha$ (TNF$\alpha$) were obtained from Sigma.

Human leukemia U937 monocyte lymphoma cells were cultured in RPMI 1640 medium supplemented with 10% FBS and 1% Penicillin-Streptomycin solution. Cells were incubated at 37° C. in a humidified atmosphere containing 5% CO2 and 95% air. Before treatment, cells were transferred into RPMI containing 1% FBS for overnight. Cells were plated on a 48 well plate. Cell culture medium included either TNFα (250 ng/mL), Triclosan(1 ppm), or both agents together or no agent (control). Cells were incubated after treatment for 24 hours. Conditioned media were collected and store at −80° C. until analysis. Samples of conditioned media were subjected to enzyme-linked immunosorbent assays (ELISA) for MMP-9, according to commercial ELISA protocol (FIG. 1).

U937 cells stimulated with TNFα produced an increase in MMP-9 level. Triclosan at 1 ppm significantly reduced MMP-9 level in TNFα stimulated U937 cells.

TABLE 1

Figure 1:
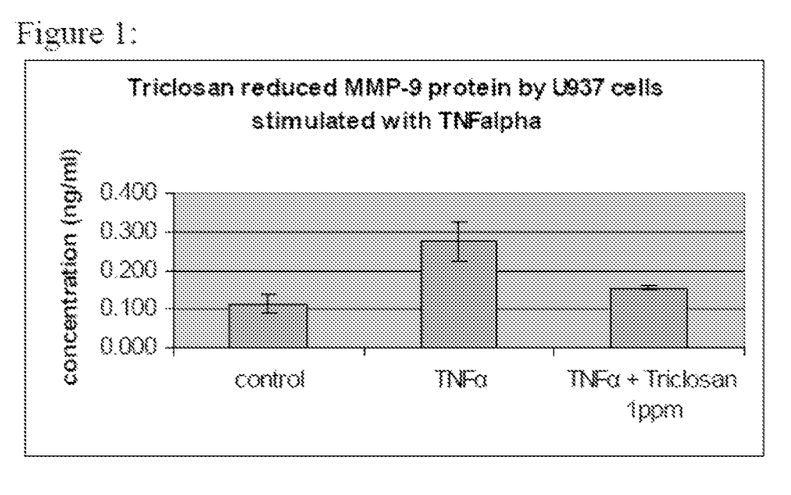
FIG. 1 illustrates the effect of 2,4,4'-trichloro-2'-hydroxydiphenyl ether on TNFα-induced MMP-9 production of monocytes.

Data for FIG. 1, demonstrating the effect of triclosan on MMP-9 production.

|  | Average (ng/ml) | Standard deviation (ng/ml) |
|---|---|---|
| control | 0.114 | 0.024333 |
| TNFα | 0.275 | 0.048665 |
| TNFα + Triclosan 1 ppm | 0.155 | 0.004867 |

Example 2

Preparation and Characterization of MMP-13

Parathyroid hormone (rat PTH 1-34) was purchased from Sigma. UMR 106-01 cells were cultured in Eagle's minimal essential medium (EMEM) supplemented with 25 mM Hepes pH 7.4, 1% nonessential amino acids, 100 units/rill penicillin, 100 µg/ml streptomycin. 5% fetal bovine serum. Real Time Quantitative RT-PCR was conducted according to the following method: UMR 106-01 cells were seeded in 12-well plates and cultured for 2-3 days in cell culture media. When cells were confluent, cell culture media was exchanged with 1% fetal bovine serum for overnight for cell starvation. Cells were pre-incubated with triclosan or a triclosan-containing dentifrice (see. e.g., U.S. Pat. Nos. 4,894,220, 5,032,386, and related patents) for 15 min and then incubated with PTH ($10^{-8}$ M) for 4 hours.

Total RNA was isolated from UMR 106-01 cells stimulated with or without PTH with TRIzol reagent. Total RNA (0.1 µg) was reverse-transcribed to cDNA using the Invitrogen SUPERSCRIPT kit according to the manufacturer's instructions. PCR was performed on cDNA using primers, the sequences of which are set forth in Table 2. All cDNAs were amplified by adding 2.5 µl of cDNA to the PCR mixture (22.5 µl) containing each primer (0.2 µM) and 12.5 µl of the Platinum SYBR Green qPCR SuperMix UDG (Invitrogen). The reactions were preincubated at 50° C. for 2 minutes to decontaminate dU-containing DNA by UDG, then at 95° C. for 2 minutes to inactivate UDG and activate Taq. The PCR program continued 49 cycles of denaturation at 95° C. for 15 seconds, annealing and elongation of the primers at 60° C. for 30 seconds. Relative quantification of gene expression was determined by using the 2-delta delta CT method where fold changes in gene expression are relative to control samples. All samples were normalized to β-actin.

All results were expressed as means±standard error (S.E.) of triplicate measurements with all experiments being repeated at least three times. Statistical analyses were carried out using the Student's t test.

UMR cells stimulated with PTH produced an increase in MMP-13 expression. Triclosan at 10 ppm, 4 ppm and 1 ppm significantly reduced MMP-13 expression in PTH stimulated UMR cells. A triclosan-containing dentifrice slurry containing 10 ppm triclosan significantly reduced MMP-13 expression in PTH stimulated UMR cells.

TABLE 2

Primer Sequences.

Rat MMP-13 gene
5'-GCCCTATCCCTTGATGCCATT-3' (sense)
5'-ACAGTTCAGGCTCAACCTGCTG-3' (antisese)

Rat-actin gene
5'-AGCCATGTACGTAGCCATCC-3' (sense)
5'-ACCCTCATAGATGGGCACAG-3' (antisese)

TABLE 3

Figure 2:
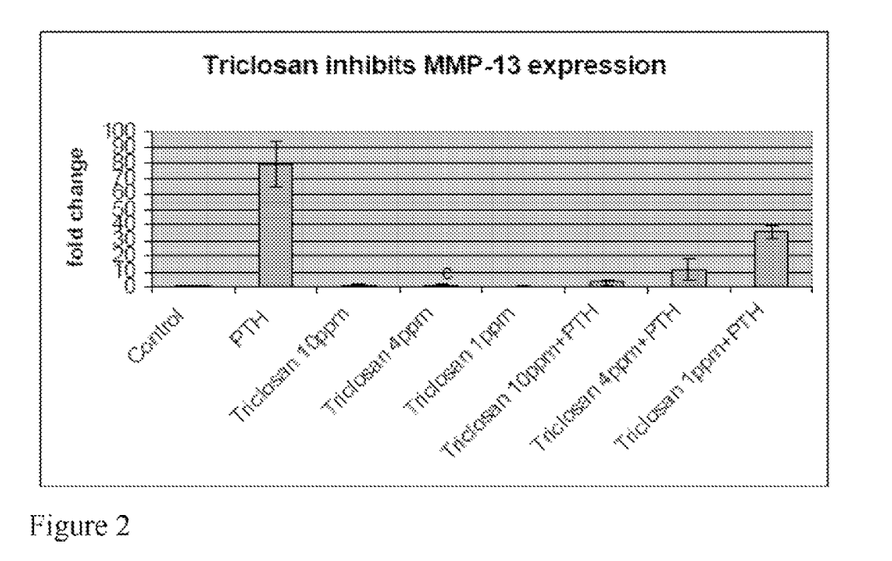
FIG. 2 illustrates the effect of 2,4,4'-trichloro-2'-hydroxydiphenyl ether on PTH-induced MMP-13 production of osteoblasts.

Data for FIG. 2 demonstrating that triclosan inhibits MMP-13 expression

|  | Average | Standard Deviation |
|---|---|---|
| Control | 0.558546 | 0.388464 |
| PTH | 78.84402 | 14.45422 |
| Triclosan 10 ppm | 1.518275 | 0.702455 |
| Triclosan 4 ppm | 1.423882 | 0.162156 |
| Triclosan 1 ppm | 0.416584 | 0.23855 |
| Triclosan 10 ppm + PTH | 3.011772 | 1.497531 |
| Triclosan 4 ppm + PTH | 10.55882 | 6.868653 |
| Triclosan 1 ppm + PTH | 35.38321 | 3.934183 |

TABLE 4

Figure 3:
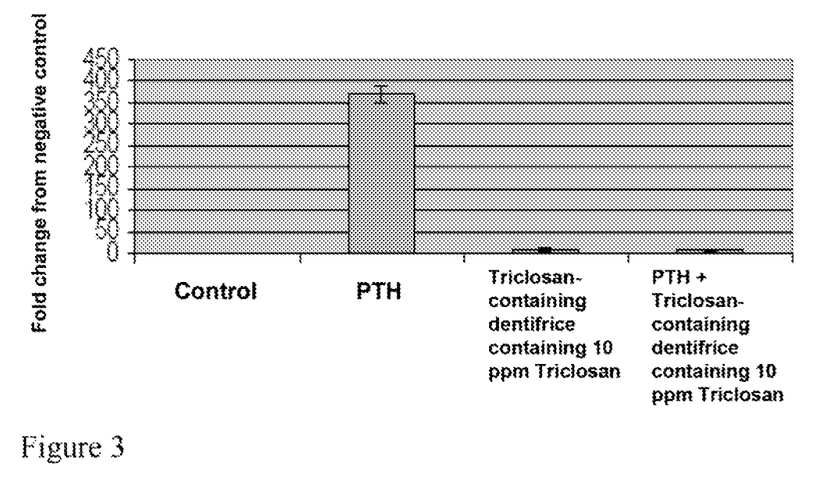
FIG. 3 illustrates the effect of a dentifrice of the present invention on PTH-induced MMP-13 production of osteoblasts.

Data for FIG. 3 demonstrating that a triclosan-containing dentifrice inhibits MMP-13 expression

|  | Average | Standard deviation |
|---|---|---|
| control | 0.917758 | 0.116307 |
| PTH | 370.6579 | 20.64484 |
| triclosan-containing dentifrice slurry containing 10 ppm Triclosan | 8.625401 | 5.675636 |
| PTH + triclosan-containing dentifrice slurry containing 10 ppm Triclosan | 7.904052 | 3.23775 |

What is claimed is:

1. A method of identifying a compound useful for treating a disease or condition of the oral cavity, the method comprising:
   obtaining a first gingival sample from a mammal suffering from a disease or condition of the oral cavity;
   obtaining a second gingival sample from the oral cavity of said mammal;
   contacting said first sample with a test compound;
   contacting said second sample with a positive control, wherein said positive control is a compound known to down-regulate the expression of one or more matrix metalloproteinases wherein said positive control is a halogenated diphenylether;
   measuring the extent to which the expression of one or more of said matrix metalloproteinases is down-regulated by said test compound;
   measuring the extent to which the expression of one or more of said matrix metalloproteinases is down-regulated by said positive control; and
   comparing the extent to which the expression of one or more of said matrix metalloproteinases is down-regulated by said test compound, with the extent to which the expression of one or more of said matrix metalloproteinases is down-regulated by said positive control;
   wherein a test compound that down-regulates the expression of one or more of said matrix metalloproteinases to an equal or greater extent than said positive control, is a compound useful in treating a disease or condition of the oral cavity.

2. The method of claim 1, wherein said one or more matrix metalloproteinases are selected from the group consisting of: MMP-8, MMP-9, and MMP-13.

3. The method of claim 1, wherein said positive control down-regulates the expression of MMP-8, MMP-9, and MMP-13.

4. The method of claim 1, wherein said disease or condition of the oral cavity is gingivitis or periodontitis.

5. The method of claim 1, wherein the positive control is triclosan.

6. The method of claim 1, wherein said test compound down-regulates the expression of one or more of said matrix metalloproteinases to a greater extent than said positive control.

7. The method of claim 1, wherein said test compound down-regulates the expression of MMP-9, and MMP-13, to a greater extent than said positive control.

8. The method of claim 1, wherein said test compound down-regulates the expression of MMP-8, MMP-9, and MMP-13, to a greater extent than said positive control.

9. The method of claim 2, wherein said positive control down-regulates the expression of MMP-8.

10. The method of claim 2, wherein said positive control down-regulates the expression of MMP-9.

11. The method of claim 2, wherein said positive control down-regulates the expression of MMP-13.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Rattus norvegicus

```
<400> SEQUENCE: 1
gccctatccc ttgatgccat t                                          21

<210> SEQ ID NO 2
<211> LENGTH: 22
<212> TYPE: DNA
<213> ORGANISM: Rattus norvegicus

<400> SEQUENCE: 2
acagttcagg ctcaacctgc tg                                         22

<210> SEQ ID NO 3
<211> LENGTH: 20
<212> TYPE: DNA
<213> ORGANISM: Rattus norvegicus

<400> SEQUENCE: 3
agccatgtac gtagccatcc                                            20

<210> SEQ ID NO 4
<211> LENGTH: 20
<212> TYPE: DNA
<213> ORGANISM: Rattus norvegicus

<400> SEQUENCE: 4
accctcatag atgggcacag                                            20
```